(12) United States Patent
Nagumo et al.

(10) Patent No.: US 9,341,582 B2
(45) Date of Patent: May 17, 2016

(54) METHOD OF GETTING TOMOGRAM USED BY X-RAY COMPUTED TOMOGRAPHY AND X-RAY COMPUTED TOMOGRAPHY SYSTEM BASED ON ITS METHOD

(71) Applicant: Hitachi, Ltd., Tokyo (JP)

(72) Inventors: Yasushi Nagumo, Tokyo (JP); Noriyuki Sadaoka, Tokyo (JP)

(73) Assignee: HITACHI, LTD., Tokyo (JP)

( * ) Notice: Subject to any disclaimer, the term of this patent is extended or adjusted under 35 U.S.C. 154(b) by 195 days.

(21) Appl. No.: 14/018,631

(22) Filed: Sep. 5, 2013

(65) Prior Publication Data
US 2014/0079180 A1    Mar. 20, 2014

(30) Foreign Application Priority Data
Sep. 20, 2012    (JP) .................................. 2012-206454

(51) Int. Cl.
  *G01N 23/04*    (2006.01)
(52) U.S. Cl.
  CPC ........ *G01N 23/046* (2013.01); *G01N 2223/419* (2013.01)
(58) Field of Classification Search
  CPC ....................... G01N 2223/419; G01N 23/046
  See application file for complete search history.

(56) References Cited

U.S. PATENT DOCUMENTS

| | | | | |
|---|---|---|---|---|
| 5,481,584 A | * | 1/1996 | Tang et al. | 378/98.9 |
| 2008/0267345 A1 | | 10/2008 | Nagumo et al. | |
| 2010/0135564 A1 | * | 6/2010 | Thomsen et al. | 382/131 |
| 2011/0243382 A1 | | 10/2011 | Morton et al. | |

FOREIGN PATENT DOCUMENTS

| | | |
|---|---|---|
| EP | 1 985 998 | 10/2008 |
| JP | 2008-275352 A | 11/2008 |
| JP | 2011-24773 A | 2/2011 |

OTHER PUBLICATIONS

European Search Report for Application No. 13182894.9, dated Feb. 5, 2014.

* cited by examiner

*Primary Examiner* — David J Makiya
*Assistant Examiner* — Dani Fox
(74) *Attorney, Agent, or Firm* — Baker Botts L.L.P.

(57) ABSTRACT

An object of this invention is to provide a tomography method and a tomography system capable of tomographic imaging targeted uniquely to the test object among subjects under test. The method involves performing a process of generating projection data about the region of interest by selecting one reference projection data set from a plurality of projection data generated in a tomography process using a plurality of X-ray energy levels and by subtracting from the reference projection data set the product of an attenuation coefficient and the transmission length of the material configuring any region other than the region of interest detected by detector elements of detectors, and performing an image reconstruction computing process to generate a tomographic or stereoscopic image of the region of interest through image reconstruction based on the projection data about the region of interest generated in the projection data generating process.

8 Claims, 9 Drawing Sheets

| NO. OF TEST OBJECT CONSTITUENT MATERIALS N | 3 |

| OK | CANCEL |

FIG. 5

| NO. OF ACCELERATING VOLTAGES USED | 3 |

| FIRST ACCELERATING VOLTAGE | 220 | (kV) |
| SECOND ACCELERATING VOLTAGE | 180 | (kV) |
| THIRD ACCELERATING VOLTAGE | 140 | (kV) |

| OK | CANCEL |

PROJECTED REGION OF MATERIALS B+C

PROJECTED REGION OF MATERIALS A+B+C

FIG. 8

PROJECTED REGION OF MATERIAL A ONLY

METHOD OF GETTING TOMOGRAM USED BY X-RAY COMPUTED TOMOGRAPHY AND X-RAY COMPUTED TOMOGRAPHY SYSTEM BASED ON ITS METHOD

CLAIM OF PRIORITY

The present application claims priority from Japanese Patent applications serial No. 2012-206454, filed on Sep. 20, 2012, the respective contents of which are hereby incorporated by reference into this application.

FIELD OF THE INVENTION

The present invention relates to a method of getting tomogram used by X-ray computed tomography and an X-ray computed tomography system based on its method.

BACKGROUND OF THE INVENTION

As one way of inspecting non-destructively internal defects of mechanical components and the like, there exists the method of transmitting X-rays into the interior of the target object to acquire images thereof (method of inspection by X-ray radiography). In particular, X-ray computed tomography systems exemplified by industrial X-ray computed tomography (CT) are capable of highly accurate tests because they can output detailed images of the interior of the target object unlike radiographic images from radiographic tests.

Also, there has been a growing need for the non-destructive inspection by X-ray computed tomography of the piping installed in power plants such as nuclear and thermal power plants, chemical plants, and oil plants. The piping of these plants is often installed in narrow locations. It is difficult to apply industrial-use X-ray computed tomography systems to the plant piping because the systems require rotating operations and have a large equipment scale. Japanese Unexamined Patent Publication No. 2008-275352 (Patent Literature 1) discloses an X-ray computed tomography method that can be applied to the plant piping. Conventional X-ray computed tomography systems perform their image reconstruction computing process based on a plurality of projection data acquired by imaging the object to be tested (called the test object hereunder) at angles of 180 degrees plus a radiation angle or at angles of 360 degrees in general, whereby tomographic or stereoscopic images are constructed. On the other hand, what is disclosed in Patent Literature 1 is a tomography method called laminography. The disclosed method involves using as a priori information such known information as shape information about the test object from among a plurality of projection data acquired at smaller angles than the angles necessary for X-ray computed tomography systems so as to perform an image reconstruction computing process supporting smaller angles, whereby tomographic or stereoscopic images can be constructed. In piping inspections that use laminography, images are acquired by having a radiation source and a radiation detector moved in parallel to the longitudinal direction of the piping.

Object examinations that use X-ray computed tomography are often targeted to test objects made up of a plurality of materials each. For example, whereas the piping inspection of a plant requires verifying the state of the piping interior, the pipes are wrapped with heat insulating materials which in turn are covered with outer castings. In piping inspections involving X-ray computed tomography, it is desired to obtain images of the piping interior for evaluation without removing the heat insulating material and outer casting. Generally, X-ray computed tomography requires positioning the entire test object within a field of vision for imaging. In image reconstruction computations for constructing tomographic images, not only the test object but also other regions need to be calculated. This requires an extensive calculating area that will increase the amount and the time of computations in addition to a growing storage area to be needed.

In view of the problems above, there have been conceived methods of using some appropriate means to estimate information about the regions other than the test object (physical properties and thicknesses of materials, etc.) and to eliminate such information. Japanese Unexamined Patent Publication No. 2011-24773 (Patent Literature 2) proposes a method of estimating the information about the regions other than the test object.

The method proposed by Patent Literature 2 involves emitting X-rays to the test object using a plurality of X-ray energy bands and, based on the measurements taken of the transmitted X-rays, obtaining the ratio of the components making up the test object. However, although this method permits acquisition of the component ratio, the thicknesses of the materials involved are not obtained. Thus Patent Literature 2 discloses little about the method of tomography targeted solely to the test object among subjects to be inspected.

It is therefore an object of the present invention to provide a tomography method and a tomography system capable of tomographic imaging targeted uniquely to the test object among subjects to be inspected.

SUMMARY OF THE INVENTION

In carrying out the present invention and according to an aspect thereof, there is provided a method including the steps of performing a material count inputting process prompting a user to input the number of materials configuring a test object; performing an X-ray energy level setting process prompting the user to input the number of X-ray energy levels and energy levels, the number of X-ray energy levels being at least equal to the number of materials configuring the test object; performing a tomography process using a plurality of X-ray energy levels to carry out X-ray radiography a plurality of times based on the numbers set in the X-ray energy level setting process; performing a transmission length calculating process to calculate the transmission length of the material configuring a region of interest and the transmission length of the material configuring any region other than the region of interest; performing a region-of-interest projection data generating process of generating projection data about the region of interest by selecting one reference projection data set from among a plurality of projection data generated in the tomography process using a plurality of X-ray energy levels and by subtracting from the reference projection data set the product of an attenuation coefficient and the transmission length of the material configuring any region other than the region of interest detected by detector elements of detectors; and performing an image reconstruction computing process to generate a tomographic image or a stereoscopic image of the region of interest through image reconstruction based on the projection data about the region of interest generated in the projection data generating process of generating projection data about the region of interest.

According to the present invention, it is thus possible to provide a tomography method and a tomography system capable of tomographic imaging targeted uniquely to the test object among subjects to be inspected.

DETAILED DESCRIPTION OF THE PREFERRED EMBODIMENTS

The present invention relates to a tomography method and a tomography system. More particularly, the invention relates to an X-ray non-destructive inspection system suitable for visually inspecting the interior of such objects as mechanical components.

First Embodiment

Explained below are examples in which the piping installed in various plants and facilities is imaged through laminography as the test object.

Figure 1:
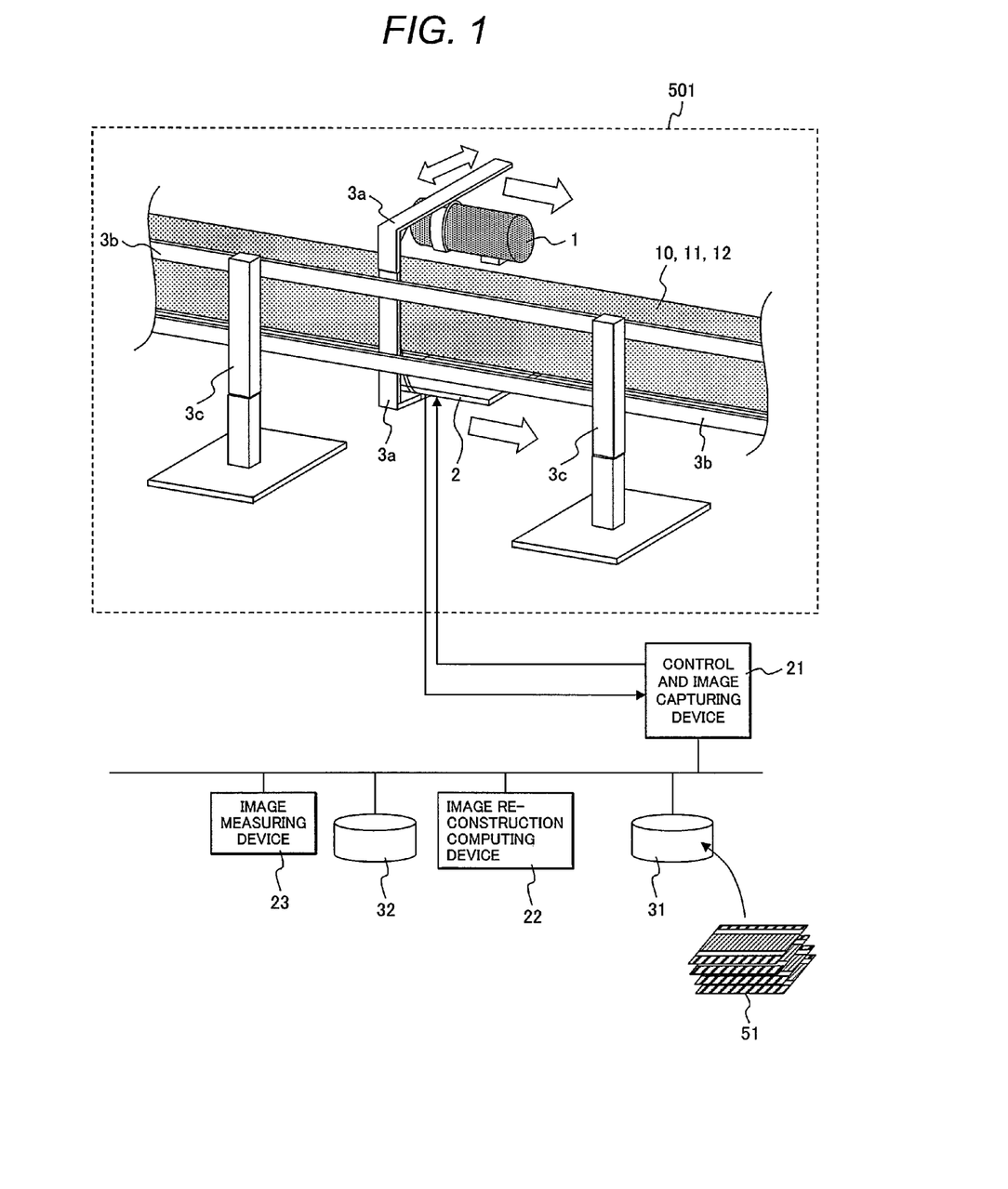
FIG. 1 is a schematic view showing a typical tomography system embodying this invention.

FIG. 1 schematically illustrates a typical X-ray computed tomography system 501 used as the first embodiment. FIG. 1 shows how the system of this embodiment is applied to a straight pipe. An X-ray source 1 and a detector 2 are positioned by a sliding mechanism 3a in a manner flanking a pipe 10 wrapped with a heat insulating material 11 and an outer casting 12. The sliding mechanism 3a is slid in the longitudinal direction of the pipe by a scanner 3b supported by supporting legs 3c. The sliding mechanism 3a is a device that slides the X-ray source 1 and detector 2 in the axial direction of the pipe 10.

The X-ray source 1 and detector 2 are moved at a constant speed. During the movement, radiograms are taken at equal intervals to acquire a plurality of projection data 51. A control and image capturing device 21 controls the capturing of projection data through the scanner 3b and detector 2. The captured projection data 51 are stored in a storage device 31 and later retrieved therefrom by an image reconstruction computing device 22 to construct tomographic or stereoscopic images. The constructed tomographic or stereoscopic images are stored in a storage device 32 and retrieved by an image measuring device 23 for defect evaluation. Here, the configuration made up of the control and image capturing device 21, storage device 31, image reconstruction computing device 22, storage device 32, and image measuring device 23 is only an example. In another example, the storage devices 31 and 32 can be the same equipment.

Figure 2:
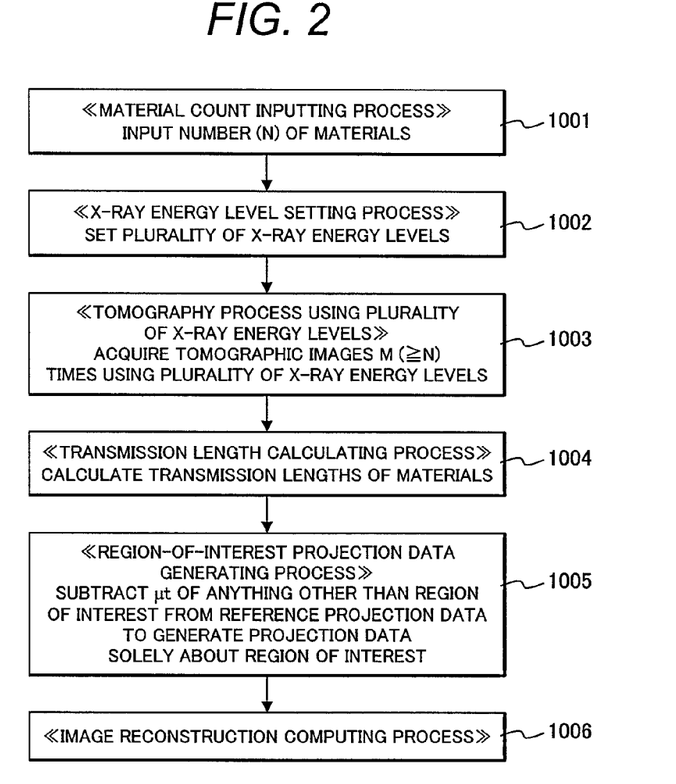
FIG. 2 is a flowchart showing a typical processing flow of a tomography method embodying this invention.
Figure 3:
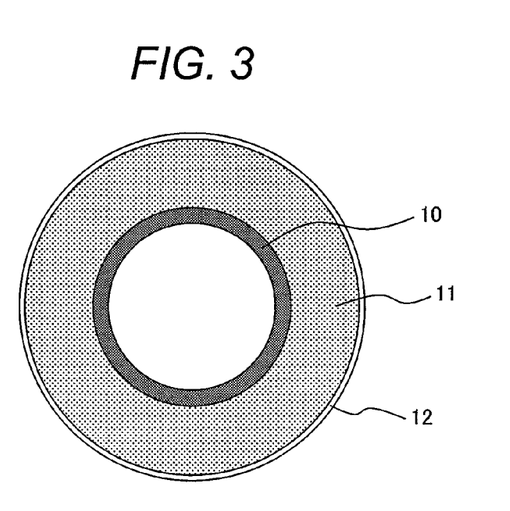
FIG. 3 is a schematic cross-sectional view of a pipe wrapped with a heat insulating material and an outer casting as the test object to be imaged by the tomography system embodying this invention.
Figure 4:
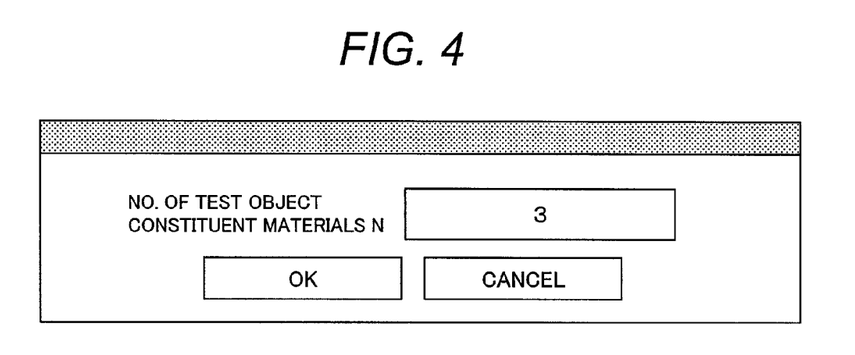
FIG. 4 is a schematic view showing a typical screen through which to input the number of materials configuring the test object, the screen being provided by the tomography system embodying this invention.

FIG. 2 shows a typical processing flow of the first embodiment. This embodiment involves carrying out a material count inputting process 1001 in which the number N of materials configuring the test object is input. FIG. 3 shows an example in which a pipe is taken as the test object. FIG. 3 is a schematic cross-sectional view of the pipe along a plane perpendicular to the central axis of the pipe. A high-temperature fluid may flow through the interior of the piping installed in plants. In order to prevent or suppress dissipation of the heat, the pipe 10 is wrapped with the heat insulating material 11 which in turn is wrapped with the outer casting 12. It can be seen that with this piping example, the number N of materials configuring the test object is three. This number is input in the material count inputting process 1001. FIG. 4 shows a typical material count input screen.

Figure 5:
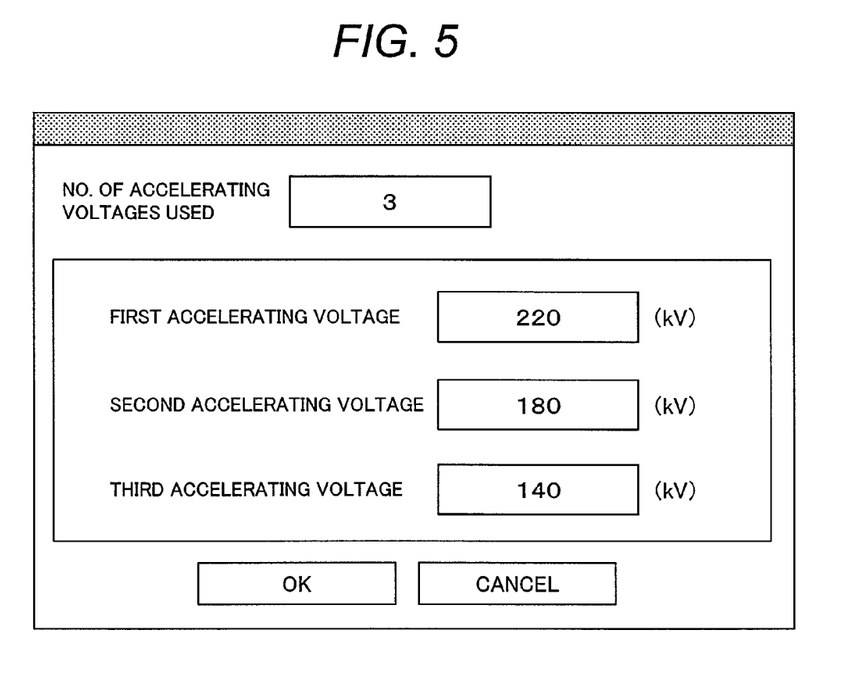
FIG. 5 is a schematic view showing a typical X-ray accelerating voltage level setting screen through which to set a plurality of X-ray energy levels, the screen being provided by the tomography system embodying this invention.

As shown in FIG. 2, following the execution of the material count inputting process 1001, an X-ray energy level setting process 1002 is carried out to set the number of X-ray energy levels and energy values for use in X-ray tomography. In the X-ray energy level setting process 1002, given the number N input in the material count inputting process 1001, the number M of X-ray energy levels that is at least equal to the number N (M≥N) is set along with each of the X-ray energy levels. Usually, the X-ray source 1 used in non-destructive inspection generates not X-rays on a single X-ray energy level but X-rays having a continuous energy spectrum. For this reason, it is easier to set electron accelerating voltages as the basis for X-ray generation than to set X-ray energy values. Thus in the X-ray energy setting process 1002, accelerating voltage values may alternatively be input in place of X-ray energy levels. FIG. 5 shows a typical setting screen for setting accelerating voltages.

Referring next to FIG. 2, a tomography process 1003 involving a plurality of X-ray energy levels is carried out using M X-ray energy levels set in the X-ray energy level setting process 1002 so as to perform tomography M times. Tomography is performed on each of the X-energy levels in accordance with the procedure explained above in connection with FIG. 1. As a specific example, tomography is carried out using X-ray radiation emitted by the X-ray source 1 operating on the initially set X-ray energy level. After reaching an end edge of the scanner 3b (or a designated position), the sliding mechanism 3a is moved to the initial imaging position. Tomography is then carried out using the secondly-set X-ray energy level. The process above is performed until acquisition of the M-th tomogram is completed. For the above example, it is assumed that the sliding mechanism 3a is moved back to the initial imaging position every time tomography is repeated. Alternatively, after the sliding mechanism 3a has reached the end edge, tomography on a different X-ray energy level may be started from that position. Carrying out the above processes causes M sets of projection data 51 acquired on the different X-ray energy levels to be stored into the storage device 31.

Figure 6:
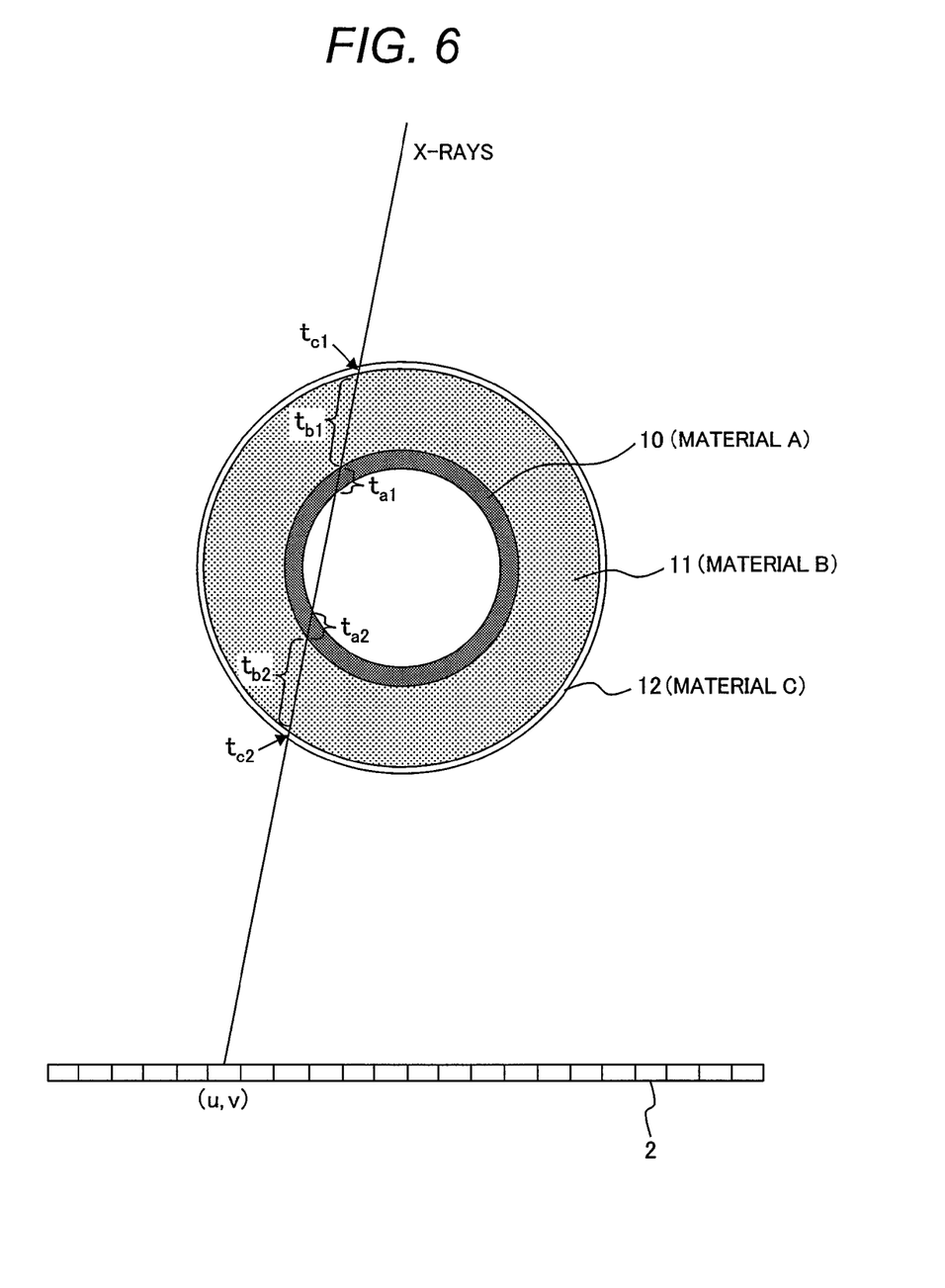
FIG. 6 is a schematic view explanatory of a transmission length calculation processing method for use with the tomography system embodying this invention.

Next, a transmission length calculating process 1004 is carried out. The transmission length calculating process 1004 involves calculating the transmission length, i.e., the length of X-rays transmitted in each of the materials configuring the test object, by use of M sets of projection data 51 acquired in the tomography process 1003 involving a plurality of X-ray energy levels. FIG. 6 depicts details of the transmission length calculating process 1004 applied to the test object that is the pipe 10 wrapped with the heat insulating material 11 and outer casting 12. As shown in FIG. 6, it is assumed that the pipe 10, the heat insulating material 11, and the outer casting 12 are called materials A, B and C, respectively. In FIG. 6, a straight line crossing these materials indicates one of X-ray permeation pathways. The detector 2 is a flat panel detector that has its detector elements arranged in a two-dimensional matrix. It is assumed here that (u,v) represents a detector element number; that $I_{u,v}$ denotes the X-ray intensity detected where the detector element in question is located, and that $P_{u,v}$ stands for the X-ray attenuation rate obtained from the X-ray intensity of interest. If it is assumed that the lengths of X-rays detected by these detector element in their locations to have been transmitted in each of the materials are represented by $t_{Au,v}$, $t_{Bu,v}$, and $t_{Cu,v}$, respectively, then the following equations (1) through (3) hold:

$$t_{Au,v} = t_{a1} + t_{a2} \quad (1)$$

$$t_{Bu,v} = t_{b1} + t_{b2} \quad (2)$$

$$t_{Cu,v} = t_{c1} + t_{c2} \quad (3)$$

If it is assumed that the X-ray energy level is $E_i$ (i=1, 2, 3) when M=N=3; the $I(E_i)_{u,v}$ denotes the X-ray intensity measured by the detector element having the detector element number (u,v), and that $I_0(E_i)_{u,v}$ represents the X-ray intensity measured in the same location without the test object, then the X-ray attenuation rate $P(E_i)_{u,v}$ is given by the following equations (4) through (6):

$$P(E_1)_{u,v} \equiv \ln(I_o(E_1)_{u,v}/I(E_1)_{u,v}) = \mu_A(E_1)t_{Au,v} + \mu_B(E_1)t_{Bu,v} + \mu_C(E_1)t_{Cu,v} \quad (4)$$

$$P(E_2)_{u,v} \equiv \ln(I_o(E_2)_{u,v}/I(E_2)_{u,v}) = \mu_A(E_2)t_{Au,v} + \mu_B(E_2)t_{Bu,v} + \mu_C(E_2)t_{Cu,v} \quad (5)$$

$$P(E_3)_{u,v} \equiv \ln(I_o(E_3)_{u,v}/I(E_3)_{u,v}) = \mu_A(E_3)t_{Au,v} + \mu_B(E_3)t_{Bu,v} + \mu_C(E_3)t_{Cu,v} \quad (6)$$

where $\mu_A(E_i)$, $\mu_B(E_i)$, and $\mu_C(E_i)$ (i=1, 2, 3) denote the attenuation coefficients of the respective materials on the X-ray energy level $E_i$. An attenuation coefficient is a physical quantity indicative of the rate at which X-rays attenuate when transmitted in a given material for a unit length while causing an interaction therewith. As such, the attenuation coefficient is dependent on X-ray energy. Since there exists a body of data about the attenuation coefficients of elements having been established with regard to X-ray energy, that body of data may be used as a database. Alternatively, X-ray attenuation tests may be carried out beforehand on specimens of the same material with their thickness t already known, and the measured values may be used to obtain the attenuation coefficient $\mu(E_i)$ using the following equation (7):

$$I(E_i) = I_o(E_i)\exp(-\mu(E_i)t) \quad (7)$$

The three equations (4) through (6) above have three unknowns $t_{Au,v}$, $t_{Bu,v}$, and $t_{Cu,v}$. By solving these simultaneous equations, it is possible to obtain the unknowns $t_{Au,v}$, $t_{Bu,v}$, and $t_{Cu,v}$ in each of the equations. Whereas the above applies when M=N, if M>N, there will be generated M equations similar to those (4) through (6). In this case, N equations may be selected and solved as simultaneous equations. When M>N, it is also possible to utilize the technique of estimating the solutions (transmission length) using the least-squares method.

The above processes are carried out on the projection data 51 in each of the imaging locations involved with all detector elements. That is, the transmission length of each material is calculated from the projection data 51 with regard to every detector element. The result of the calculations is stored in the storage device 31 or 32.

Referring next to FIG. 2, a region-of-interest projection data generating process 1005 is carried out to generate projection data 52 about solely the test object part (called the region of interest hereunder) based on the result of the transmission length calculating process 1004. Here, from the M sets of projection data 51 acquired using M X-ray energy levels, one set of projection data 51 is selected as the reference projection data. The projection data about the region of interest is generated by subtracting from the reference projection data the product of the attenuation coefficient and transmission length of any material other than that of the region of interest in the respective detector element positions (u,v). In the ensuing description, as in the explanation of the transmission length calculating process 1004, a specific explanation will be made of the case of the pipe 10 (material A) wrapped with the heat insulating material 11 (material B) and outer casting 12 (material C). It is assumed here that one set of projection data 51 imaged on the X-ray energy level $E_1$ is the reference projection data. Using the transmission lengths $t_B$ and $t_C$ of the materials B and C and their attenuation coefficients $\mu_B(E_i)$ and $\mu_C(E_i)$ on the X-ray energy level $E_1$ following their acquisition in the transmission length calculating process 1004, the projection data about the region of interest (projection data $P_A(E_1)_{u,v}$ about the material A only) is generated by the following equation (8):

$$P_A(E_1)_{u,v} = P(E_1)_{u,v} - (\mu_B(E_1)t_{Bu,v} + \mu_C(E_1)t_{Cu,v}) = \mu_A(E_1)t_{Au,v} \quad (8)$$

Figure 7:
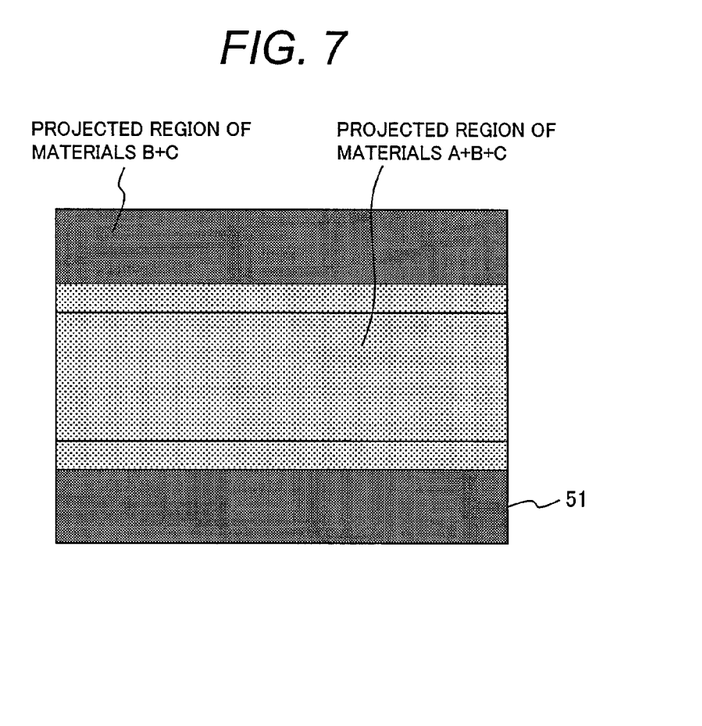
FIG. 7 is a schematic view showing typical projection data about the test object to which the method of this invention has yet to be applied in conjunction with the tomography system embodying the invention.
Figure 8:
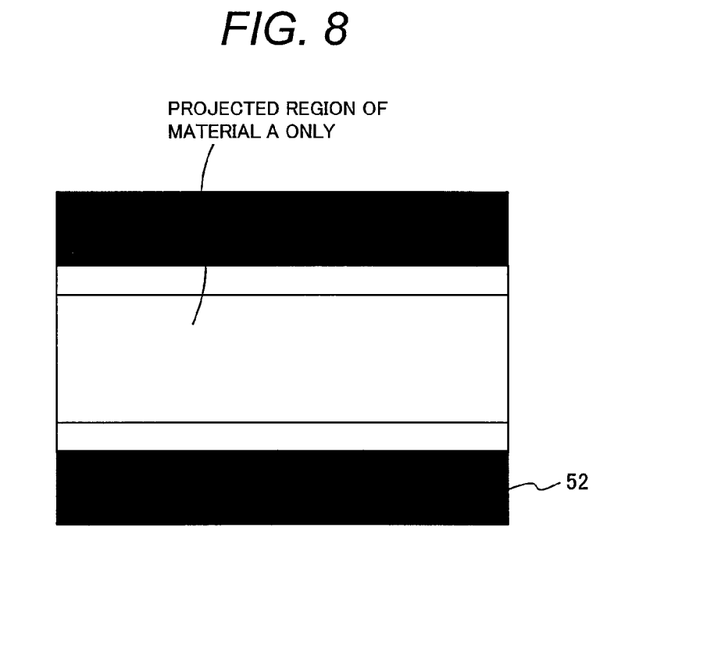
FIG. 8 is a schematic view showing typical projection data obtained solely about the region of interest using the method of this invention in conjunction with the tomography system embodying the invention.

The above processes are carried out on all detector elements with the projection data 51 regarding the respective imaging locations. FIGS. 7 and 8 show examples in which these processes have been practiced. FIG. 7 shows one set of projection data 51 obtained by imaging the pipe 10 (material A) furnished with the heat insulating material 11 (material B) and outer casting 12 (material C) using the X-ray energy level $E_1$. FIG. 8 shows a result from having applied the region-of-interest projection data generating process 1005 to the projection data. As shown in FIG. 8, practicing the region-of-interest projection data generating process 1005 makes it possible to generate the projection data 52 solely about the region of interest.

Figure 9:
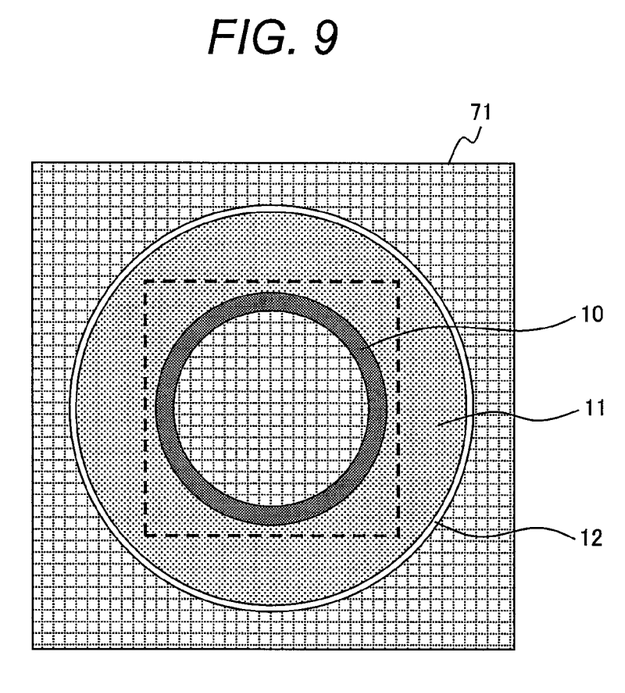
FIG. 9 is a schematic view showing a typical conventional reconstructed image to which a series of processing steps of the method embodying this invention has not been applied.
Figure 10:
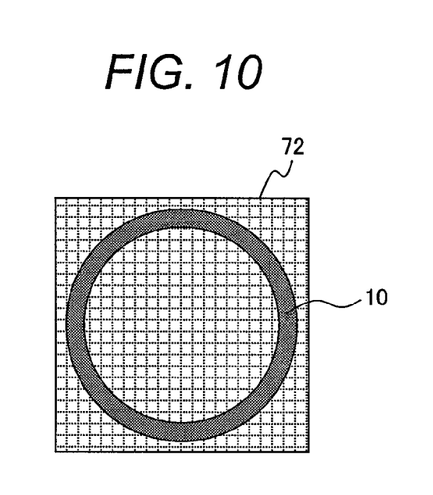
FIG. 10 is a schematic view showing a typical reconstructed image to which the processing method of the tomography system embodying this invention is applied.

An image reconstruction computing process 1006 is carried out using as its input data the projection data 52 only about the region of interest generated in the region-of-interest projection data generating process 1005. The process 1006 generates a reconstructed image 72 regarding the region of interest alone. FIG. 9 shows a reconstructed image 71 as a comparative example to which the processing of this embodiment has not been applied, and FIG. 10 shows the reconstructed image 72 to which the processing of this embodiment has been applied. In the case of the comparative example in FIG. 9, an image reconstructing region needs to be set in a manner including the heat insulating material 11 and outer casting 12 in addition to the pipe 10 that is the test object (region of interest). That is, calculations also need to be performed with regard to the regions outside a dotted-line square indicating the region of interest. It can be seen that the amount of calculations to be performed on the portions that are originally unnecessary adds to the calculations on the test object. On the other hand, FIG. 10 shows a portion corresponding to the inside of the dotted-line square indicated in FIG. 9. As shown in FIG. 10, practicing the processing of this embodiment makes it possible to limit the image reconstructing region to the pipe 10 that is the region of interest, which contributes to appreciably reducing the amount of the calculations involved.

The X-ray source 1 applied to the system operating on the above method may be an X-ray source for use in ordinary non-destructive inspections (a source with its X-ray focus size on the order of millimeters). Alternatively, a high-resolution microfocus X-ray source with its focus size on the order of tens of microns may be utilized.

Also, if the X-ray source 1 is of a type that can change the X-ray energy levels (i.e., accelerating voltages) at high speed, then it is possible to acquire images on as many as M X-energy levels instantaneously in each of different imaging locations. That means the scanning with the X-ray source 1 and detector 2 can be performed only once instead of M times.

The above-described method makes it possible to perform tomography aimed at only the test object among subjects to be tested. It is also possible to suppress an unnecessary increase in the amount of calculations, calculation time, and storage area.

Second Embodiment

Figure 11:
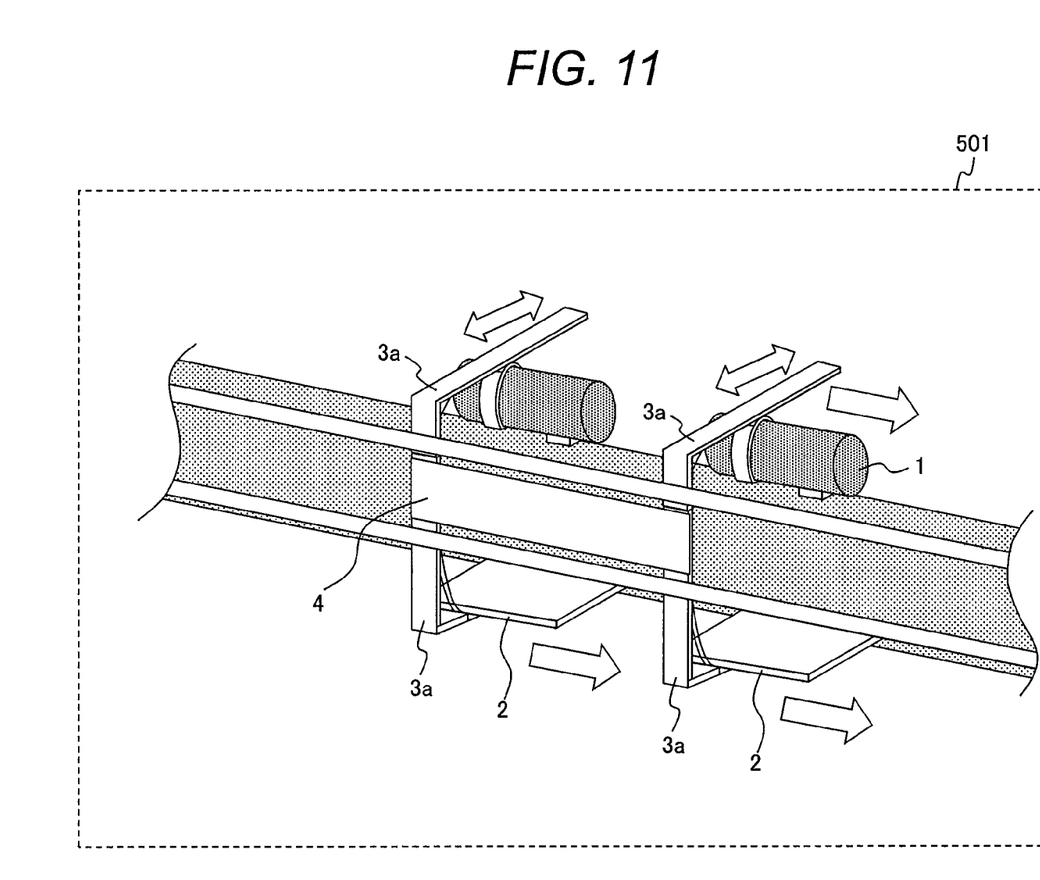
FIG. 11 is a schematic view showing a typical tomography system as a second embodiment of this invention.

FIG. 11 shows a system practiced as the second embodiment of this invention. What is shown in FIG. 11 is approximately the same configuration as that of the X-ray computed tomography system 501 as the first embodiment, except that there are two sets of X-ray sources 1 and detectors 2. These two sets are connected by a connecting plate 4. They are positioned in the axial direction of the test object and moved by the sliding mechanism 3a for simultaneous scanning. The two sets of X-ray sources 1 and detectors 2 are fixed by the connecting plate 4 in such a manner that the distance between the two sets is L (L is any natural number) times the interval between two imaging positions (imaging pitch) $\Delta x$. With this arrangement, the second set of X-ray source 1 and detector 2 can image the same positions of the test object as the first set during scanning. That is, when the first set advances by $L\Delta x$ following imaging of a given position P of the test object, the second set reaches the same position P to image it. Where the X-ray source 1 of the first set operates on a given X-ray energy level $E_1$ and the X-ray source 1 of the second set operates on a different X-ray energy level $E_2$, it is possible to reduce the scanning count and thereby shorten the imaging time involved.

In the preceding paragraphs, two sets of X-ray sources 1 and detectors 2 have been explained. Alternatively, three or more sets of X-ray sources 1 and detectors 2 may be used. As with the first embodiment, the imaging time can be further shortened by utilizing a type of X-ray source capable of changing accelerating voltages at high speed. Naturally, a microfocus X-ray source may also be adopted for high-resolution imaging.

Third Embodiment

Explained below is an example in which an industrial X-ray computed tomography system is used to image the test object.

Figure 12:
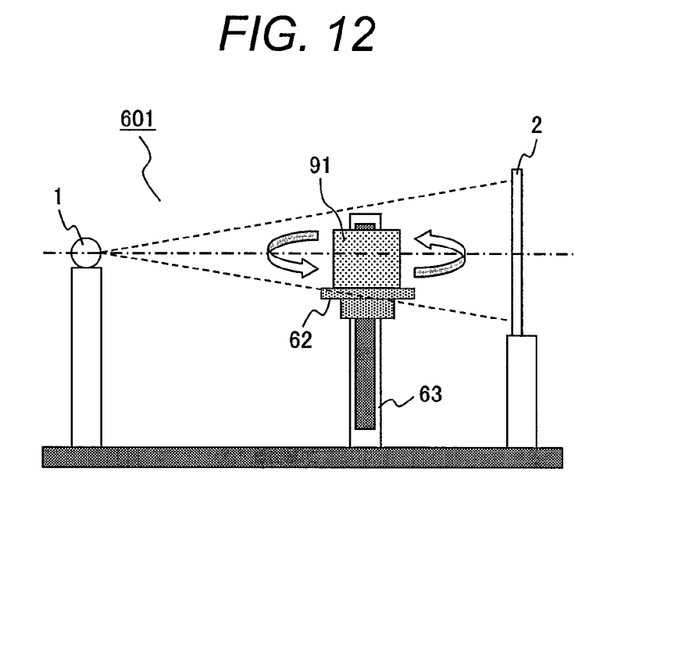
FIG. 12 is a schematic view showing a typical tomography system as a third embodiment of this invention.

FIG. 12 shows a typical X-ray computed tomography system 601 used as the third embodiment. The X-ray computed tomography system 601 is made up of an X-ray source 1, a flat-shaped detector 2 positioned opposite to the X-ray source 1, a rotating table 62 positioned between the X-ray source 1 and the detector 2 and carrying a test object 91, and a control device (not shown) that controls these components. In imaging the test object 91, the rotation of the rotating table 62 is synchronized with the detector 2 capturing the projection data at intervals of a constant rotation angle pitch. The test object 91 is imaged at angles of 180 degrees plus a radiation angle or at angles of 360 degrees. The rotating table 62 is structured in such a manner that its height may be changed by an up-down stage 63 so as to image an elevated test object 91.

Figure 13:
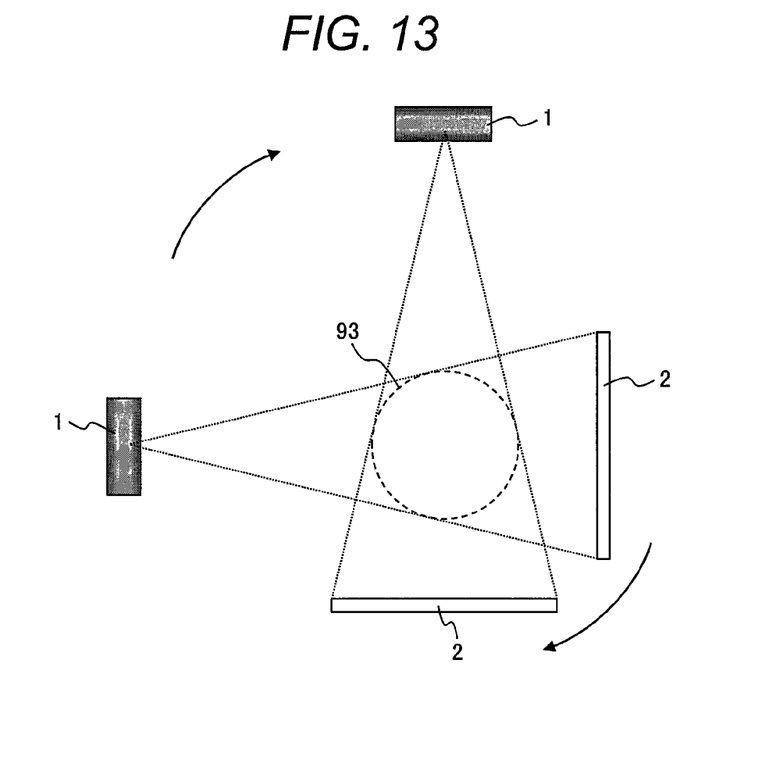
FIG. 13 is a schematic view showing a field of view for imaging by the tomography system as the third embodiment of this invention.
Figure 14:
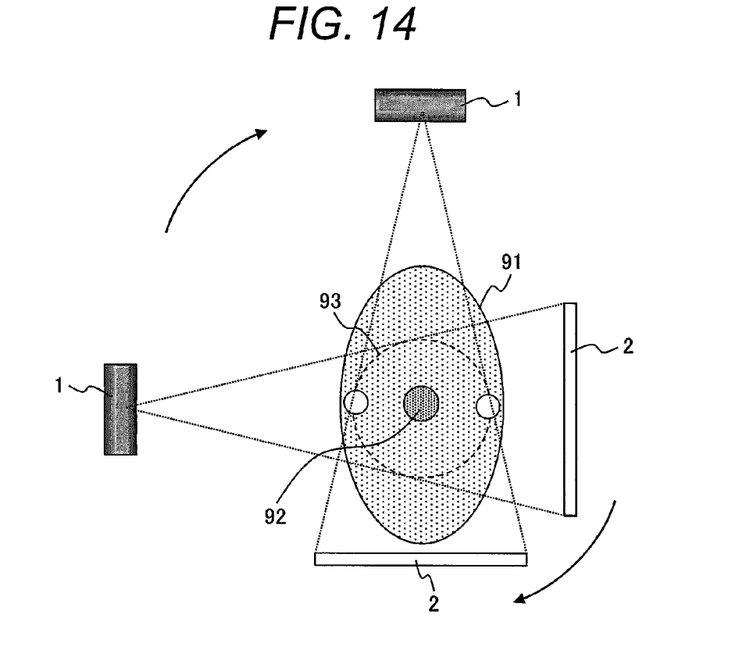
FIG. 14 is a schematic view showing how a test object sticking out of the imaging field of view is imaged by the tomography system as the third embodiment of this invention.
Figure 15:
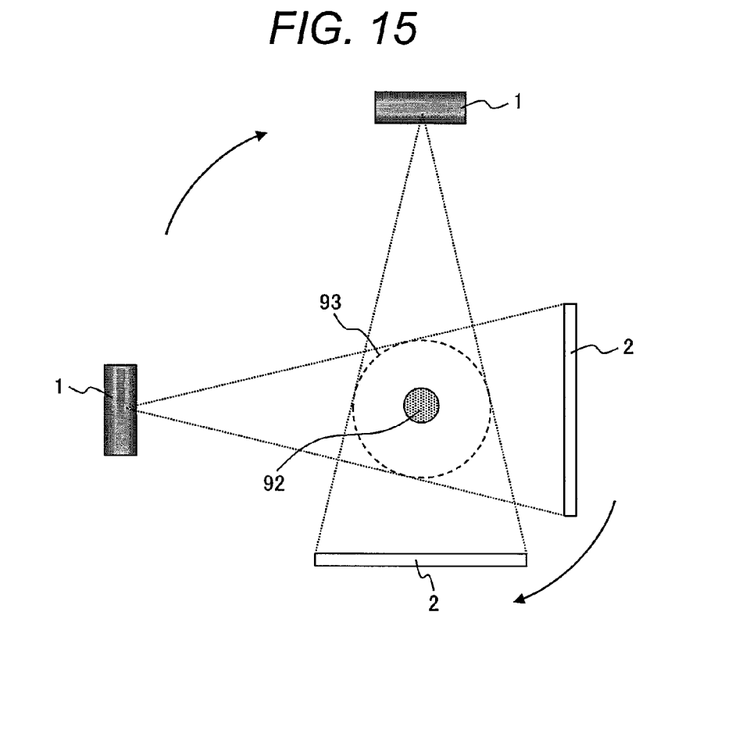
FIG. 15 is a schematic view showing how a test object sticking out of the imaging field of view is imaged by an imaging method of the tomography system as the third embodiment of this invention, the view configuring a tomogram equivalent to what is obtained when the processing of this invention is applied.

For the industrial X-ray computed tomography system to carry out tomography of the test object conventionally requires that the entire test object be contained within the imaging field of view. FIG. 13 shows an example of an imaging field of view 93 for the industrial X-ray computed tomography system. In FIGS. 13 through 15, the X-ray source 1 and detector 2 are assumed to rotate around the test object 91 that is fixed. There is no problem with this setup since computed tomography need only be considered in terms of relative motions between the test object on the one hand and the radiation source and detector on the other hand. The imaging field of view 93 is the range in which tomograms can be constructed. It is difficult to carry out tomography of any object not contained within this range. One such example is shown in FIG. 14. In FIG. 14, a horizontal cross section of the test object 91 is shown larger than the imaging field of view 93. In the case of FIG. 14, a region of interest 92 is found in the imaging field of view 93 but the test object as a whole cannot be contained therein. That means the conventional industrial X-ray computed tomography system is incapable of reconstructing a cross-sectional view of the test object. However, based on the number of materials N configuring the test object (N is 3 in the case of FIG. 14), tomography may be carried out using M ($\geq$N) X-ray energy levels, and the processes of the procedure discussed in conjunction with the first embodiment may be performed on the projection data 51. This makes it possible to generate a reconstructed image equivalent to a tomogram solely of the region of interest shown in FIG. 15.

With the third embodiment, as with the first embodiment, it is possible to use a microfocus X-ray source or a type of X-ray source that can change accelerating voltages at high speed. And as with the second embodiment, it is also possible for the third embodiment to implement an X-ray computed tomography system that includes a plurality of sets of X-ray sources 1 and detectors 2.

The above-described method permits tomography aimed at only the test object among subjects to be tested. The method can also suppress an unnecessary increase in the amount of calculations, calculation time, and storage area.

Using the method and system of the present invention makes it possible to perform tomography aimed at only the test object among subjects to be tested. It is also possible for the method and system to suppress an unnecessary increase in the amount of calculations, calculation time, and storage area in the image reconstruction computing process.

What is claimed is:

1. An X-ray computed tomography method for use with an X-ray computed tomography system having an X-ray source emitting X-rays to a test object, detectors installed opposite to each other in a manner flanking the test object, a control and image capturing device controlling the capture of projection data about the X-rays transmitted through the test object, a storage device storing a plurality of the projection data acquired by the detectors, and an image reconstruction computing device retrieving a plurality of the projection data from the storage device to perform image reconstruction computations in order to generate a tomographic image or a stereoscopic image, the X-ray computed tomography method comprising the steps of:
   performing a material count inputting process prompting a user to input the number of materials configuring the test object;
   performing an X-ray energy level setting process prompting the user to input the number of X-ray energy levels and energy levels, the number of X-ray energy levels being at least equal to the number of materials configuring the test object;
   performing a tomography process using a plurality of X-ray energy levels to carry out X-ray radiography a plurality of times based on the numbers set in the X-ray energy level setting process;
   performing a transmission length calculating process to calculate the transmission length of the material configuring a region of interest and the transmission length of the material configuring any region other than the region of interest;
   performing a region-of-interest projection data generating process of generating projection data about the region of interest by selecting one reference projection data set from among a plurality of projection data generated in the tomography process using a plurality of X-ray energy levels, wherein the selected reference projection data set is an X-ray attenuation rate at one energy level, and by subtracting from the reference projection data set the product of an attenuation coefficient and the transmission length of the material configuring any region other than the region of interest detected by detector elements of the detectors; and
   performing an image reconstruction computing process to generate a tomographic image or a stereoscopic image of the region of interest through image reconstruction based on the projection data about the region of interest generated in the projection data generating process of generating projection data about the region of interest.

2. An X-ray computed tomography method according to claim 1, wherein the X-ray source is made up of a plurality of X-ray sources each emitting X-rays on a different energy level and positioned in the axial direction of the test object, the detectors being positioned opposite to each other across each of the X-ray sources.

3. An X-ray computed tomography method according to claim 1, wherein the X-ray source is capable of emitting X-rays while changing the X-ray energy level.

4. An X-ray computed tomography method according to any of claims 1 to 3, wherein the X-ray source is a microfocus X-ray source.

5. An X-ray computed tomography system having an X-ray source emitting X-rays to a test object, detectors installed opposite to each other in a manner flanking the test object, a control and image capturing device controlling the capture of projection data about the X-rays transmitted through the test object, a storage device storing a plurality of the projection data acquired by the detectors, and an image reconstruction computing device retrieving a plurality of the projection data from the storage device to perform image reconstruction computations in order to generate a tomographic image or a stereoscopic image, the X-ray computed tomography system further comprising:
   a material count inputting means for prompting a user to input the number of materials configuring the test object;
   an X-ray energy level setting means for prompting the user to input the number of X-ray energy levels and energy levels, the number of X-ray energy levels being at least equal to the number of materials configuring the test object;
   a tomography means which uses a plurality of X-ray energy levels for carrying out X-ray radiography a plurality of times based on the numbers set by the X-ray energy level setting means;
   a transmission length calculating means for calculating the transmission length of the material configuring a region of interest and the transmission length of the material configuring any region other than the region of interest, the material configuring the test object;
   a region-of-interest projection data generating means which generates projection data about the region of interest by selecting one reference projection data set from among a plurality of projection data generated by the tomography means using a plurality of X-ray energy levels, wherein the selected reference projection data set is an X-ray attenuation rate at one energy level, and by subtracting from the reference projection data set the product of an attenuation coefficient and the transmission length of the material configuring any region other than the region of interest detected by detector elements of the detectors; and
   an image reconstruction computing means for generating a tomographic image or a stereoscopic image of the region of interest through image reconstruction based on the projection data about the region of interest generated by the projection data generating means of generating projection data about the region of interest.

6. An X-ray computed tomography system according to claim 5, wherein the X-ray source is made up of a plurality of X-ray sources each emitting X-rays on a different energy level and positioned in the axial direction of the test object, the detectors being positioned opposite to each other across each of the X-ray sources.

7. An X-ray computed tomography system according to claim 5, wherein the X-ray source is capable of emitting X-rays while changing the X-ray energy level.

8. An X-ray computed tomography system according to any of claims 5 to 7, wherein the X-ray source is a microfocus X-ray source.

* * * * *